United States Patent [19]

Wermuth et al.

[11] Patent Number: 4,596,802
[45] Date of Patent: Jun. 24, 1986

[54] THIADIAZOLE DERIVATIVES ACTIVE ON THE CENTRAL NERVOUS SYSTEM AND PHARMACEUTICAL COMPOSITIONS

[75] Inventors: Camille G. Wermuth, Strasbourg; Roger Brodin, Montpellier; Paul Worms, Saint Gely du Fesc, all of France

[73] Assignee: Sanofi, Paris, France

[21] Appl. No.: 786,465

[22] Filed: Oct. 11, 1985

[30] Foreign Application Priority Data

Oct. 18, 1984 [FR] France ............................ 84 15991

[51] Int. Cl.⁴ .................. A61K 31/535; C07D 413/12
[52] U.S. Cl. ...................................... 514/230; 544/134
[58] Field of Search ........................ 544/134; 514/230

[56] References Cited

U.S. PATENT DOCUMENTS 3,419,575 12/1968 Griss .................................. 544/134
3,919,428 11/1975 Eberle ................................ 514/363

FOREIGN PATENT DOCUMENTS 2092714 1/1972 France .

OTHER PUBLICATIONS

Journal of Pharmaceutical Sciences, vol. 64, No. 7, Jul. 1975, pp. 1250–1252, Washington, U.S.; Lalezari et al.

Primary Examiner—Robert W. Ramsuer
Attorney, Agent, or Firm—Bacon & Thomas

[57] ABSTRACT

The invention relates to thiadiazole derivatives corresponding to the formula:

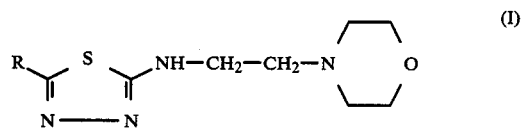

in which R represents:
  a linear or branched alkyl group having from 1 to 5 carbon atoms;
  a cycloalkyl group having 5 or 6 carbon atoms;
  a phenyl group optionally substituted by 1 or 2 halogen atoms, preferably chlorine, by 1 or 2 lower alkyl or lower alkoxy groups, by 1 or 2 hydroxyl groups or by a nitro or trifluoromethyl group;
  a biphenylyl group; or
  an alpha-naphthyl group;

and the pharmaceutically acceptable salts of the said derivatives. It also relates to a process for the preparation of the said derivatives and the pharmaceutical compositions in which they are present. The said derivatives act on the central nervous system.

16 Claims, No Drawings

THIADIAZOLE DERIVATIVES ACTIVE ON THE CENTRAL NERVOUS SYSTEM AND PHARMACEUTICAL COMPOSITIONS

The present invention relates, by way of new products, to thiadiazole derivatives possessing valuable properties on the central nervous system. It also relates to a process for the preparation of the said derivatives and the pharmaceutical compositions in which they are present.

More precisely, the compounds according to the invention correspond to the general formula:

$$R-\underset{N-N}{\underset{\|}{C}}\underset{}{\overset{S}{\diagdown}}\underset{}{\underset{\|}{C}}-NH-CH_2-CH_2-N\underset{}{\diagup}\underset{}{\diagdown}O \qquad (I)$$

in which R represents:
- a linear or branched alkyl group having from 1 to 5 carbon atoms;
- a cycloalkyl group having 5 or 6 carbon atoms;
- a phenyl group optionally substituted by 1 or 2 halogen atoms, preferably chlorine, by 1 or 2 lower alkyl or lower alkoxy groups, by 1 or 2 hydroxyl groups or by a nitro or trifluoromethyl group;
- a biphenylyl group; or
- an alpha-naphthyl group.

The salts which the compounds of the formula (I) form with pharmaceutically acceptable mineral or organic acids are an integral part of the invention.

In the present Application, lower alkyl or lower alkoxy groups are understood as meaning alkyl or alkoxy groups containing from 1 to 5 carbon atoms.

Compounds similar to the compounds according to the invention have been described in the chemical literature. Thus, Journal of Pharmaceutical Sciences 64 (7), 1250–1252 (1975) mentions compounds corresponding to the formula:

$$R_1-\underset{N-N}{\underset{\|}{C}}\underset{}{\overset{S}{\diagdown}}\underset{}{\underset{\|}{C}}-NH-CH_2-CH_2-N\underset{R'}{\overset{R'}{\diagup}} \qquad (II)$$

in which R' represents a methyl or ethyl group and $R_1$ represents a tolyl, methoxyphenyl or nitrophenyl group.

These compounds are described as possessing antihistaminic and anticholinergic properties.

Surprisingly, it has been found that the compounds of the prior art possess to only a very slight extent the properties on the central nervous system which the compouns according to the invention possess.

The compounds according to the invention can be prepared from the 2-halogeno-1,3,4-thiadiazoles appropriately substituted in the 5-position, according to the equation:

$$R-\underset{N-N}{\underset{\|}{C}}\underset{}{\overset{S}{\diagdown}}\underset{}{\underset{\|}{C}}-X + NH_2-CH_2-CH_2-N\underset{}{\diagup}\underset{}{\diagdown}O \longrightarrow (I)$$

1                       2

(X = Cl or Br)

The reaction is carried out by heating the 2 reactants in a solvent such as an alkanol like ethanol or n-butanol. The most common procedure is to use an excess of the amine 2 in order to fix the hydracid formed during the reaction.

Finally, if X is chlorine, it is possible to facilitate the reaction by carrying it out in the presence of potassium iodide.

The compound (I) is isolated by extraction into a dilute acid medium and the aqueous solution is rendered alkaline to free the base. If appropriate, the product isolated in this way can be converted to a salt by the usual methods.

If R represents a hydroxyphenyl or dihydroxyphenyl group, the compounds (I) are obtained by demethylation of the corresponding compounds (I) in which R represents a methoxyphenyl or dimethoxyphenyl group, by a known process, for example by heating with concentrated hydrobromic acid.

The halogenated starting materials 1 are known or can be prepared by known methods. Thus, the products 1 can be obtained from the corresponding amino compounds:

$$R-\underset{N-N}{\underset{\|}{C}}\underset{}{\overset{S}{\diagdown}}\underset{}{\underset{\|}{C}}-NH_2 \longrightarrow R-\underset{N-N}{\underset{\|}{C}}\underset{}{\overset{S}{\diagdown}}\underset{}{\underset{\|}{C}}-X$$

3                       1 by diazotization and decomposition of the diazonium salt in the presence of the hydracid XH by the methods described in Chemische Berichte 89, 1534–1543 (1956) and Tetrahedron 24, 3209–3217 (1968).

The amino compounds 3 are known or can be prepared by known processes [Journal of Pharmaceutical Society of Japan 72, 373–375 (1952); Journal of the Chemical Society (1949), 1163–1167; and Canadian Journal of Chemistry 37, 1121–1123 (1959)], which consist in converting the acid RCOOH or the acid chloride RCOCl to the corresponding thiosemicarbazide and in cyclizing the latter with a dehydrating agent such as sulfuric acid.

The non-limiting examples which follow will provide a clearer understanding of the invention.

EXAMPLE 1

2-(2-Morpholinoethylamino)-5-phenyl-1,3,4-thiadiazole dihydrochloride.

(I R=$C_6H_5$); SR 95311 A.

The 2-chloro-5-phenyl-1,3,4-thiadiazole used as the starting material is prepared as indicated in Tetrahedron 24, 3214 (1968).

5.2 g of 2-morpholinoethylamine and 0.01 g of potassium iodide are added to a solution of 3.93 g of 2-chloro-5-phenyl-1,3,4-thiadiazole in 30 ml of butan-1-ol.

The mixture is heated under reflux for 2 hours, with stirring, and the solvent is then removed in vacuo. The residue is taken up in ethyl acetate and the organic solution is extracted with a 10% aqueous solution of hydrochloric acid. The aqueous phase is rendered alkaline to pH 8–9 by the addition of sodium bicarbonate. Extraction is carried out with ethyl acetate and the organic solution is washed twice with water and then dried over magnesium sulfate. The solvent is evaporated off in vacuo. The oily residue is dissolved in the minimum quantity (3 to 4 ml) of hot isopropanol, and 2 ml of concentrated hydrochloric acid solution are then added to the isopropanol solution.

The colorless precipitate which separates out is filtered off, dried in vacuo and recrystallized from methanol.

A colorless solid is finally obtained. Weight: 2.9 g; melting point: 222°–224° C.

The same product is obtained if the starting chlorine derivative is replaced by an equivalent quantity of the corresponding bromine derivative, in which case it is not necessary to add potassium iodide.

EXAMPLE 2

2-(2-Morpholinoethylamino)-5-cyclohexyl-1,3,4-thiadiazole.

(I R=$C_6H_{11}$); SR 43058.

(a) 2-Amino-5-cyclohexyl-1,3,4-thiadiazole.

25.6 g of cyclohexanecarboxylic acid, 21 ml of concentrated sulfuric acid and 15.2 g of thiosemicarbazide are mixed, with cooling in a water-bath. The mixture is then heated at 90°–100° C. for 15 hours, with stirring.

After cooling, the mixture is poured into 400 ml of cold water and an insoluble material is separated off. The aqueous solution is rendered alkaline with 150 ml of concentrated aqueous ammonia. The precipitate is filtered off, washed with water, dried and recrystallized from ethanol. Melting point: 254°–256° C.; weight: 14 g.

(b) 2-Bromo-5-cyclohexyl-1,3,4-thiadiazole.

A finely ground, intimate mixture of 60 g of sodium nitrite and 13.8 g of 2-amino-5-cyclohexyl-1,3,4-thiadiazole is added in small portions, over about 1 hour, to a suspension of 2.6 g of copper powder in 200 ml of 48% hydrobromic acid solution, cooled to −20° C.

The temperature is kept at between −20° and −10° C. throughout the whole of the addition. When the addition has ended, the cooling bath is removed and the mixture is stirred at room temperature for 2 hours and then at 40°–45° C. for 1 hour 30 minutes. It is left to stand overnight, 500 ml of water are then added and extraction is carried out with ethyl acetate. The organic phase is washed with an aqueous solution of sodium chloride and then neutralized by the addition of concentrated sodium hydroxide solution. The organic phase is decanted, washed with an aqueous solution of sodium chloride and dried over magnesium sulfate. The solvent is evaporated off to dryness. The remaining oil (13 g) solidifies slowly and is to be used as such for the next step.

(c) SR 43058.

The procedure followed in Example 1 is applied to the bromine derivative obtained above.

In this case, the base obtained when the aqueous phase is rendered alkaline with sodium bicarbonate crystallizes after evaporation of the solvent.

The product is therefore not converted to a salt but recrystallized from isopropyl ether. Melting point: 102°–104° C.

EXAMPLES 3 to 16

The products (I) shown in the table which follows are obtained by following the procedure used in the previous examples, but varying the starting material.

TABLE I

R—C(=N—N=)—S—C(=NH—CH₂—CH₂—N(morpholino))

| SR code no. | R | Base or salt | Melting point °C. (solvent of crystallization) |
|---|---|---|---|
| 43055 A | —CH₃ | hydrochloride | 246–248 (ethanol) |
| 43056 A | (H₃C)₂CH—CH₂— | dimaleate | 105–107 (isopropanol) |
| 43057 A | cyclobutyl | maleate | 156–158 (ethanol) |
| 95340 A | 4-Cl-C₆H₄— | dihydrochloride | 235–237 (methanol) |
| 95396 A | 3-Cl-C₆H₄— | dihydrochloride | 240–242 (methanol) |
| 95397 A | 2-Cl-C₆H₄— | dihydrochloride | 235–240 (methanol) |
| 95371 A | 4-H₃C-C₆H₄— | dihydrochloride | 217–219 (methanol) |
| 43531 A | 3-CF₃-C₆H₄— | dihydrochloride | 210 (ethanol-methanol) |
| 43604 | 4-F₃C-C₆H₄— | base | 135 (methanol) |
| 43530 | 4-O₂N-C₆H₄— | base | 224 (ethanol) |
| 43198 | 4-H₃CO-C₆H₄— | base | 110–112 (ethanol) |
| 43295 | 3,4-(H₃CO)₂-C₆H₃— | base | 122–124 (ethyl acetate) (with 1H₂O) |
| 43294 | biphenyl-4-yl | base | 160–162 (ethanol) (with 0.5H₂O) |

TABLE I-continued

R—⟨S⟩—NH—CH₂—CH₂—N⟨O⟩ (with N—N in thiadiazole ring)

| SR code no. | R | Base or salt | Melting point °C. (solvent of crystallization) |
|---|---|---|---|
| 95559 A | naphthyl | dihydrochloride | 175–177 (methanol) |

EXAMPLE 17

2-(2-Morpholinoethylamino)-5-(4-hydroxyphenyl)-1,3,4-thiadiazole dihydrochloride.

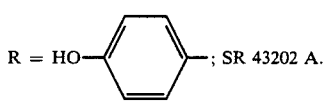

R = HO—⟨phenyl⟩—; SR 43202 A.    (I)

A mixture of 7.1 g of 2-(2-morpholinoethylamino)-5-(4-methoxyphenyl)-1,3,4-thiadiazole (SR 43198, Example 13) and 150 ml of 48% hydrobromic acid solution is heated under reflux for 20 hours, with stirring.

200 ml of 30% sodium hydroxide solution are added. The aqueous phase is washed with 500 ml of ethyl acetate, 500 ml of saturated ammonium chloride solution are then added and the mixture is left for 2 hours, with stirring. The precipitate is filtered off and washed with water. The solid is dissolved in 100 ml of ethanol, and 9.2 ml of concentrated hydrochloric acid are added. The hydrochloride is filtered off and recrystallized from methanol.

This gives 5 g of the dihydrochloride, which crystallizes with 0.5 molecule of water; melting point=250°–252° C.

EXAMPLE 18

2-(2-Morpholinoethylamino)-5-(3,4-dihydroxyphenyl)-1,3,4-thiadiazole dihydrochloride.

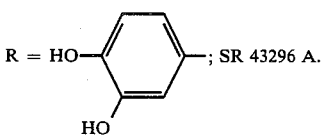

R = HO—⟨phenyl⟩—(HO)—; SR 43296 A.    (I)

The procedure used in Example 17 is applied to 2-(2-morpholinoethylamino)-5-(3,4-dimethoxyphenyl)-1,3,4-thiadiazole (SR 43295, Example 14).

SR 43296 A is obtained in the same way; melting point=161°–163° C.; it crystallizes with 1 molecule of water.

The compounds according to the invention were studied for their therapeutic properties and more especially their activity on the central nervous system.

In this study, the products according to the invention were compared with 2 similar compounds substituted in the 2-position by a dialkylaminoethylamino chain identical to that of the compounds known in the prior art.

These compounds correspond to the formulae:

Compound A: phenyl—⟨thiadiazole⟩—NH—CH₂—CH₂—N(CH₃)₂, 2HCl

Compound B: phenyl—⟨thiadiazole⟩—NH—CH₂—CH₂—N(C₂H₅)₂, 2HCl

ACUTE TOXICITY

The products to be studied were administered intraperitoneally in increasing doses to groups of 10 mice (CD1, Charles River; 20±1 g). The mortality caused by the products studied was noted for 24 hours following the administration of the product.

From the results obtained, the 50% lethal dose, i.e. the dose causing the death of 50% of the animals, was determined for each of the products studied.

All the products according to the invention have a 50% lethal dose greater than or equal to 300 mg/kg, whereas the mortality of the comparison compounds at a dose of 300 mg/kg is 70% in the case of compound A and 90% in the case of compound B.

ANTAGONISM OF THE PTOSIS INDUCED BY RESERPINE

This test, described by GOURET et al. (Journal de Pharmacologie, Paris, 8, 333–350, 1977), was performed on female CD1 mice (Charles River) weighing 20±1 g. Reserpine causes ptosis 1 hour after intravenous administration; the majority of antidepressants oppose this ptosis.

The following protocol was chosen. The substances to be studied were administered intraperitoneally and the reserpine was simultaneously administered intravenously at a dose of 2 mg/kg. One hour after the administration of reserpine, the number of animals not exhibiting ptosis was noted.

This test was performed on groups of 10 mice; the results are expressed as $ED_{50}$ (50% effective dose), i.e. the dose which completely blocks the ptosis induced by reserpine in 50% of the animals.

The results obtained with various products according to the invention were as follows:

| | | |
|---|---|---|
| SR 95311 A | $ED_{50}$: | 4.6 mg/kg |
| SR 95340 A | $ED_{50}$: | 8.8 mg/kg |
| SR 95396 A | $ED_{50}$: | 11.3 mg/kg |
| SR 95397 A | $ED_{50}$: | 18 mg/kg |
| SR 43058 | $ED_{50}$: | 22 mg/kg |
| SR 43057 A | $ED_{50}$: | 23 mg/kg |

The comparison products gave the following results under the same conditions:

| | | |
|---|---|---|
| Compound A | $ED_{50}$: | 32 mg/kg |
| Compound B | $ED_{50}$: | 43 mg/kg |

POTENTIATION OF THE TREMBLING INDUCED BY L-5-HTP

L-5-HTP (L-5-hydroxytryptophan) is the biosynthesis precursor of serotonin. Its injection into mice causes a behavioral syndrome characterized in particular by violent trembling. Antidepressants which inhibit the recapture of serotonin or monoamine oxidase inhibitors (MAOI) potentiate this effect of L-5-HTP (LESSIN, 1959).

The protocol described by LESSIN (Biochem. Pharmacol., 2, 290–298, 1959) was used. The products to be studied were administered intraperitoneally to female CD1 mice (Charles River; 20±1 g) 1 hour before an intraperitoneal injection of L-5-HTP at a dose of 200 mg/kg (maximum dose which does not induce trembling). The absence or presence of distinct trembling was observed for the next 20 minutes.

The results are expressed as $ED_{50}$, i.e. the dose which induces trembling in 50% of the animals treated. The following results were obtained:

| | | |
|---|---|---|
| SR 95311 A | $ED_{50}$: | 6 mg/kg |
| SR 95340 A | $ED_{50}$: | 3.6 mg/kg |
| SR 43058 | $ED_{50}$: | 17 mg/kg |
| SR 43056 A | $ED_{50}$: | 12 mg/kg |
| SR 95397 A | $ED_{50}$: | 14.5 mg/kg |
| SR 43531 A | $ED_{50}$: | 7.8 mg/kg |
| SR 43530 | $ED_{50}$: | 6.2 mg/kg |
| SR 43198 | $ED_{50}$: | 7 mg/kg | whereas the $ED_{50}$ of the 2 comparison products is greater than 60 mg/kg.

ROTATION BEHAVIOR

This test is the one described by PROTAIS et al. (Journal de Pharmacologie, Paris, 7, 251–255, 1976). Female mice (Charles River, CD1) weighing from 25 to 30 g were subjected beforehand to a unilateral lesion of the striatum by the stereotaxic injection of 6-hydroxydopamine at a rate of 8 μg per animal. One week after this operation, the products were administered intraperitoneally to groups of 7 mice. 1 hour after administration of the product, the number of rotations was evaluated for 2 minutes. The rotations on the same side as the lesion were counted as positive and those on the opposite side as negative.

The algebraic sum of the rotations for one group of treated animals was compared with that of the group of control animals which had only received the vehicle (aqueous solution of gum).

In this test, stimulants of the dopaminergic receptors (apomorphine type) reduce the spontaneous rotations whereas indirect dopaminomimetic agents (amphetamine type) increase them.

The results are expressed as MED (minimum effective dose), i.e. the minimum dose necessary to cause a significant reduction (Student's t-test) in the number of ipsilateral rotations spontaneously observed in the control animals.

The following results were obtained:

| | |
|---|---|
| SR 95311 A | MED: 0.1 mg/kg |
| SR 95396 A | MED: 0.1 mg/kg |
| SR 95397 A | MED: 0.1 mg/kg |
| SR 43604 | MED: 0.1 mg/kg |
| SR 43530 | MED: 0.1 mg/kg |
| SR 43202 A | MED: 0.1 mg/kg |
| SR 43295 | MED: 0.1 mg/kg |
| SR 43296 A | MED: 0.1 mg/kg |
| SR 43294 | MED: 0.1 mg/kg |
| SR 95559 A | MED: 0.1 mg/kg | whereas the MED of the 2 comparison products is greater than 2 mg/kg.

These results show that the products according to the invention possess antidepressant and dopaminomimetic properties coupled with a very favorable chemotherapeutic index.

Consequently, the products according to the invention can be used in human therapy for a variety of neurological and psychiatric complaints: treatment of mood disorders and behavioral disorders, neurotic and endogenous depressions, memory disorders in the elderly, infantile hyperkinesis, autism, psychogenic sexual insufficiency and Parkinson's disease.

These products can be administered orally or parenterally.

Thus, the present Application also relates to the pharmaceutical compositions containing a compound according to the invention as the active ingredient, in combination with a pharmaceutically acceptable vehicle.

The dosage can vary within wide proportions, in particular depending on the type and severity of the complaint to be treated and depending on the method of administration. In general, the adult dosage by oral administration will vary between 1 and 500 mg per day, in one or more individual doses.

An example of a pharmaceutical preparation which may be indicated is gelatin capsules containing:

| | |
|---|---|
| SR 95311 A | 50 mg |
| Aerosil | 0.5 mg |
| Magnesium stearate | 1.5 mg |
| Starch STA RX 1500 | 48 mg |
| | 100 mg |

What is claimed is:

1. A thiadiazole derivative correponding to the formula:

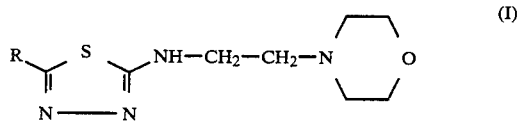

in which R represents:
a linear or branched alkyl group having from 1 to 5 carbon atoms;
a cycloalkyl group having 5 or 6 carbon atoms;
a phenyl group optionally substituted by 1 or 2 halogen atoms, by 1 or 2 lower alkyl or lower alkoxy groups, by 1 or 2 hydroxyl groups or by a nitro or trifluoromethyl group;
a biphenylyl group; or
an alpha-naphthyl group;
and the pharmaceutically acceptable salts of the said derivative.

2. A thiadiazole derivative as claimed in claim 1, wherein R represents a linear or branched alkyl group having from 1 to 5 carbon atoms.

3. A thiadiazole derivative as claimed in claim 1, wherein R represents a cycloalkyl group having 5 or 6 atoms.

4. A thiadiazole derivative as claimed in claim 1, wherein R represents a phenyl group optionally substituted by 1 or 2 halogen atoms, by 1 or 2 lower alkyl or lower alkoxy groups, by 1 or 2 hydroxyl groups or by a nitro or trifluoromethyl group.

5. A thiadiazole derivative as claimed in claim 1, wherein R represents a biphenylyl group.

6. A thiadiazole derivative as claimed in claim 1, wherein R represents an alpha-naphthyl group.

7. A thiadiazole derivative as claimed in claim 4, wherein the phenyl group is optionally substituted by 1 or 2 chlorine atoms.

8. A thiadiazole derivative as claimed in claim 1, in the form of a dihydrochloride salt, and wherein R is phenyl.

9. A thiadiazole derivative as claimed in claim 1, which is the dihydrochloride and wherein R is a 4-chlorophenyl group.

10. A thiadiazole derivative as claimed in claim 1, which is the dihydrochloride and wherein R is a 3-chlorophenyl group.

11. A thiadiazole derivative as claimed in claim 1, which is a dihydrochloride and R is a 2-chlorophenyl group.

12. A thiadiazole derivative as claimed in claim 1, which is a dihydrochloride and wherein R is a 3-trifluorophenyl group.

13. A thiadiazole derivative as claimed in claim 1, wherein R is a 4-nitrophenyl group.

14. A thiadiazole derivative as claimed in claim 1, wherein R is a 4-methoxyphenyl group.

15. A thiadiazole derivative as claimed in claim 1, which is the dihydrochloride and wherein R is a 4-hydroxyphenyl group.

16. A pharmaceutical composition which contains a thiadiazole derivative as claimed in claim 1 as the active ingredient, in combination with a pharmaceutically acceptable vehicle.

* * * * *